US010828466B2

(12) United States Patent
Yokota

(10) Patent No.: US 10,828,466 B2
(45) Date of Patent: Nov. 10, 2020

(54) CATHETER ASSEMBLY

(71) Applicant: TERUMO KABUSHIKI KAISHA, Tokyo (JP)

(72) Inventor: Takayuki Yokota, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 151 days.

(21) Appl. No.: 16/262,767

(22) Filed: Jan. 30, 2019

(65) Prior Publication Data

US 2019/0160263 A1 May 30, 2019

Related U.S. Application Data

(63) Continuation of application No. PCT/JP2017/028310, filed on Aug. 3, 2017.

(30) Foreign Application Priority Data

Aug. 4, 2016 (JP) ................................ 2016-153600

(51) Int. Cl.

*A61M 25/06* (2006.01)
*A61L 29/06* (2006.01)
*A61L 29/14* (2006.01)
*A61M 25/00* (2006.01)

(52) U.S. Cl.

CPC ......... *A61M 25/0606* (2013.01); *A61L 29/06* (2013.01); *A61L 29/14* (2013.01); *A61M 25/06* (2013.01); *A61M 2025/0006* (2013.01)

(58) Field of Classification Search

CPC ........ A61B 17/320016; A61B 17/3478; A61B 17/3496; A61M 25/06; A61M 25/0606
See application file for complete search history.

(56) References Cited

U.S. PATENT DOCUMENTS

2003/0204169 A1 10/2003 Howell et al.

FOREIGN PATENT DOCUMENTS

JP 2002-045423 A 2/2002
JP 2005-523117 A 8/2005
JP 2015-047493 A 3/2015

OTHER PUBLICATIONS

International Searching Authority, "International Search Report," issued in connection with International Patent No. PCT/JP2017/028310, dated Oct. 10, 2017.
International Searching Authority, "Written Opinion," issued in connection with International Patent Application No. PCT/JP2017/028310, dated Oct. 10, 2017.
Translation of the Written Opinion of the International Searching Authority dated Oct. 10, 2017 in corresponding application No. PCT/JP2017/028310.

*Primary Examiner* — Deanna K Hall
(74) *Attorney, Agent, or Firm* — Foley & Lardner LLP

(57) ABSTRACT

A catheter assembly includes: a catheter having an inner cavity; and an inner needle retractably located in the inner cavity of the catheter. The inner needle includes: a barrel, a blade surface located distal of the barrel and being inclined with respect to a center axis of the inner needle, and an inner needle side locking surface located at least at a portion of an outer surface linking the barrel with the blade surface. An inner surface of the catheter includes a catheter side locking surface in contact with the inner needle side locking surface such that relative movement of the catheter in a proximal direction with respect to the inner needle is restricted.

20 Claims, 10 Drawing Sheets

12
20
20a
52
50
64a (64)
24
33
57 (64)
24a (26)
58a
58
60 (61)
62 (63)
22
56
57 (64)
57a
54
60b
60a
50a 10
70
40a
40
20a
22
24
20
12
54
50

12
22
52
20a
20
50
57
(64)
56
64a
(64)
57a
24
33
54
57
(64)
50a
24a (26)
58a
58
62
(63)
60
(61)
60b
60a 12
20a
50a
22
52
IVD
IVC
IVB
IVA
32
64a
(64)
28
33
30
24
56
20
31
57
(64)
56a
X1
24a
(26)
50
54a
62
54
Y2
58a
(58)
Y1
60b
60a 13
52
20a
20
50
22
57
(64)
56
64a
(64)
24
33
57a
54
57
(64)
24a (26)
50a
58a
58
62
(63)
60
(61)
60b
60a 14
22
52
20a
20
50
65 (64)
56
64a (64)
57a
24
59
33
54
57 (64)
50a
24a (26)
58a
62 (63)
58
60 (61)
60b
60a 20a
50a
22
52
32A
64a
(64)
65
(64)
59
24
56
30
28
31A
20
57
(64)
56a
33
Y3
50
54a
54
62
Y2
14
58a
(58)
60b
60a 15
52
20a
20
50
22
24
24a (26)
66a
(66)
54
58
62
(63)
60
(61)
60b
60a 15
20a
50a
22
52
24
66a
34
66
24a
20
50
58a
54
58
60b
60a 24
22
16
20
57
(64)
33
35
58
58a
24a
50
31
28
67 (64)
54
56
52

24
22
17
64a
(64)
57
(64)
20
58
58a
24a
50
36
54
56
52

24
22
18
68
(64)
20
58
58a
24a
50
37
54
56
52

CATHETER ASSEMBLY

CROSS-REFERENCE TO RELATED APPLICATIONS

This is a bypass continuation of PCT Application No. PCT/JP2017/028310, filed on Aug. 3, 2017, which claims priority to Japanese Application No. 2016-153600, filed on Aug. 4, 2016. The contents of these application are hereby incorporated by reference in their entireties.

BACKGROUND

The present disclosure relates to a catheter assembly including a multiple structure needle having an inner needle inserted through a catheter and exposed from a distal end of the catheter.

BACKGROUND ART

A catheter assembly is used in construction of an introduction part of an infusion line in a patient at infusion. As disclosed in JP 2015-47493 A, a catheter assembly has a double structure needle having a structure in which an inner needle is inserted through a catheter with a needle tip exposed from the distal end of the catheter. In use of the catheter assembly, a user punctures a patient's body with the double structure needle, advances the catheter into the blood vessel, and thereafter extracts the inner needle from the catheter while holding the catheter in place.

This type of catheter assembly includes a flexible catheter so as to facilitate insertion and placement of the catheter in the patient's body. A flexible catheter, however, is liable to shrink due to time lapse or an influence of the external environment, and occurrence of shrinkage in the axial direction might cause retraction of the distal end of the catheter with respect to the inner needle. This might result in an increase in the amount of protrusion of the inner needle from the distal end of the catheter, and thus, the user tends to focus on insertion of the catheter and tend to perform deep puncture with the needle. Deep puncture with the needle in this manner might lead to a possibility that the needle tip of the inner needle pierces into a blood vessel inner wall, making it difficult to perform insertion of the catheter in some cases.

SUMMARY

Certain embodiments described in the present disclosure have been made in view of the above circumstances and aim to provide a catheter assembly capable of suppressing retraction of the distal end of the catheter with a simple configuration so as to steadily reduce the amount of protrusion of an inner needle protruding from the catheter, enabling satisfactory insertion of the catheter into a living body.

In one embodiment, a catheter assembly includes: a catheter having an inner cavity extending along a center axis of the catheter; and an inner needle retractably inserted through the inner cavity, in which the inner needle includes: a barrel; a blade surface provided distal of the barrel and inclined with respect to a center axis of the inner needle; and an inner needle side locking surface provided at least at a portion of an outer surface linking the barrel with the blade surface, an inner surface of the catheter including a catheter side locking surface in contact with the inner needle side locking surface in an assembled state in which the inner needle is inserted through the inner cavity, and a state of the inner needle side locking surface and the catheter side locking surface being in contact with each other in the assembled state restricts relative movement of the catheter in the proximal direction with respect to the inner needle.

According to the above embodiment, with a simple configuration in which the inner needle side locking surface and the catheter side locking surface are in contact with each other in an assembled state, the catheter assembly can suppress retraction of the distal end of the catheter. That is, the catheter side locking surface is caught on the inner needle side locking surface in the assembled state, leading to a state in which relative movement of the catheter in the proximal direction with respect to the inner needle is constantly restricted. With this configuration, it is possible to maintain the amount of protrusion of the inner needle protruding from the catheter even with occurrence of shrinkage in the catheter, enabling the user to insert the catheter satisfactorily into the living body.

In one aspect, the inner needle includes an intermediate surface formed between the inner needle side locking surface and the blade surface so as to allow the inner needle side locking surface and the intermediate surface to form a recess that is recessed inward in a radial direction with respect to the barrel.

With the inner needle having a recess that is recessed inward in the radial direction with respect to the barrel, it is possible to facilitate contact of the catheter side locking surface with the inner needle side locking surface in the assembled state. Accordingly, this enables the catheter assembly to reliably restrict the retraction of the distal end of the catheter.

In one aspect, each of the inner needle side locking surface and the catheter side locking surface is orthogonal to the center axis of the inner needle.

This configuration enables the inner needle side locking surface and the catheter side locking surface to be caught further firmly in the axial direction of the inner needle, enabling the catheter assembly to firmly restrict the relative movement of the catheter in the proximal direction.

In one aspect, the intermediate surface is parallel to the center axis of the inner needle.

With this configuration, the catheter assembly can increase an extending length of the inner needle side locking surface extending from the proximal end of the intermediate surface, and the catheter can be more easily locked. In addition, when the inner needle is extracted from the catheter, the intermediate surface is guided to the inner surface of the catheter, enabling smooth retraction of the inner needle.

In one aspect, an inner peripheral portion of the catheter has a bulging portion protruding inward in the radial direction, and the catheter side locking surface may preferably be formed in the bulging portion.

With the catheter having the bulging portion, it is possible to allow the bulging portion to be easily caught on the inner needle side locking surface, enabling restriction of the relative movement of the catheter in the proximal direction further reliably.

In one aspect, the inner needle side locking surface extends in a ring shape around the center axis of the inner needle with the outer diameter being reduced in the distal direction, the catheter side locking surface has an inner diameter that is reduced in the distal direction, and a minimum inner diameter of the catheter side locking surface is smaller than a maximum outer diameter of the inner needle side locking surface.

Even with a configuration in which the outer diameter of the inner needle side locking surface is reduced toward the distal direction while the minimum inner diameter of the catheter side locking surface is smaller than the maximum outer diameter of the inner needle side locking surface, the catheter assembly can reliably lock the distal end of the catheter onto the inner needle.

In one aspect, a distal most end of the catheter is located at the proximal end of the blade surface in the assembled state.

With this location, the catheter assembly allows protrusion of the blade surface alone from the distal most end of the catheter, making it possible to further reduce the amount of protrusion of the inner needle without losing the puncture function of the blade surface.

In one aspect, the catheter is formed of a material containing polyurethane.

With the catheter formed of a material containing polyurethane, it is possible, in manufacturing the catheter, to adopt a manufacturing method in which the catheter is processed into a desired shape with a method of pressing the catheter against a heated mold or the like. Thereafter, the catheter may be covered with a tubular material and heated to be formed into a shape that conforms to shape of the inner needle or a transition portion of the inner needle. According to this manufacturing method, thermal shrinkage caused by heating occurs in the catheter, making it possible to bring the inner needle side locking surface and the catheter side locking surface into contact with each other further reliably.

According to certain embodiments, the catheter assembly suppresses retraction of the distal end of the catheter with a simple configuration so as to maintain the amount of protrusion of an inner needle protruding from the catheter, enabling satisfactory insertion of the catheter into the living body.

DETAILED DESCRIPTION

Hereinafter, preferred embodiments of a catheter assembly according to the present invention will be described in detail with reference to the accompanying drawings.

The catheter assembly described in the present disclosure may be used for forming an introduction part of an infusion agent or a blood transfusion agent at the time of performing infusion, transfusion, or the like on a patient (living body). Examples of the catheter assembly include a peripheral venous catheter, a peripheral arterial catheter, a central venous catheter, a PICC, and a midline catheter. The configuration according to the present invention is not limited to the catheter described above and can be applied to various devices (for example, syringes) for incising a living tissue with an inner needle and inserting a catheter to the internal portion of the living tissue.

Figure 1:
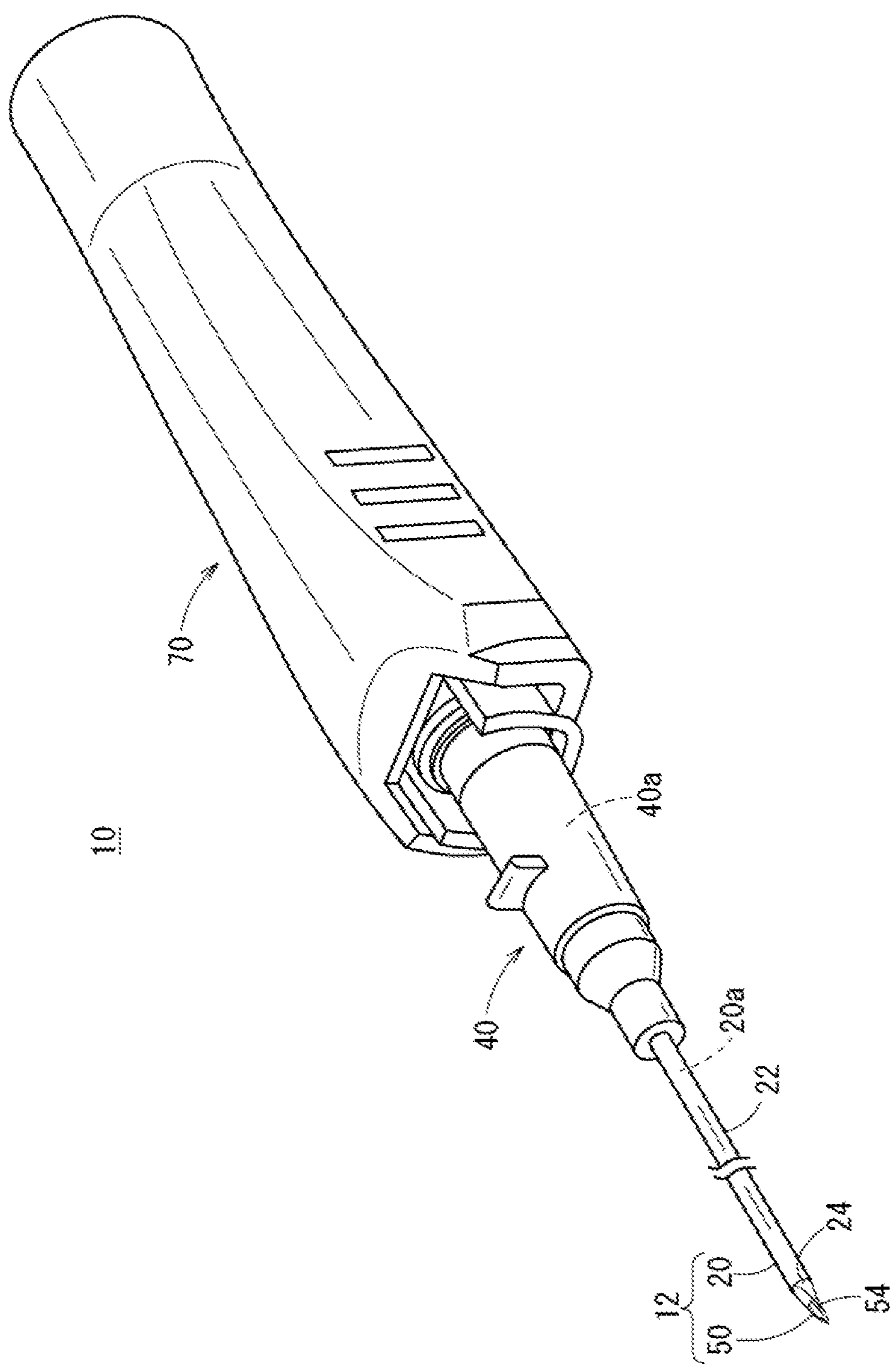
FIG. 1 is a perspective view illustrating an entire configuration of a catheter assembly according to an embodiment of the present invention.

As illustrated in FIG. 1, a catheter assembly 10 according to one embodiment of the present invention includes a catheter 20, a catheter hub 40 for fixedly holding the catheter 20, an inner needle 50, a needle hub 70 for fixedly holding the inner needle 50. Then, the catheter assembly 10 includes a double structure needle 12 having the catheter 20 overlapped with the inner needle 50 (inner needle 50 is inserted through the catheter 20) in an assembled state. Note that the needle of the catheter assembly 10 may have a multiple structure in which three or more members (for example, the catheter 20, the inner needle 50, and a guide wire (not illustrated) are overlapped in order from the outer side.

In use of the catheter assembly 10, a vein of a patient is punctured with the double structure needle 12 and the catheter 20 is inserted intravenously, and thereafter, the inner needle 50 is pulled out from the catheter 20. This allows the catheter 20 to be inserted intravenously, while allowing the proximal side of the catheter 20 and the catheter hub 40 to be exposed on the patient's skin. Subsequently, an infusion tube (not illustrated) is connected to the proximal end of the catheter hub 40, making it possible to supply an infusion agent or the like to the patient via this infusion tube.

The catheter 20 is a tubular body having appropriate levels of flexibility, and constitutes an outer needle in the above-described double structure needle 12. The interior of the catheter 20 includes an inner cavity 20*a* extending along the center axis of the catheter 20 and penetrating the distal end and the proximal end of the catheter 20. The inner cavity 20*a* is formed to have a diameter capable of accommodating the inner needle 50 and capable of allowing flow of an infusion agent or the like.

The catheter 20 includes: an outer needle side barrel 22 formed long in an axial direction and constituting a major part of the catheter 20; and a tapered portion 24 protruding short in a distal direction from a distal end of the outer needle side barrel 22.

The outer needle side barrel 22 extends in the axial direction with a constant outer diameter. The inner cavity 20*a* of the outer needle side barrel 22 is formed to be slightly larger than the outer diameter of the inner needle 50. The proximal end portion of the outer needle side barrel 22 is fixed to the distal end portion inside the catheter hub 40 using an appropriate fixing method such as fusion bonding, adhesion, and caulking. In addition, a proximal end opening (not illustrated) communicating with the inner cavity 20*a* is provided at the proximal end of the outer needle side barrel 22. The length of the outer needle side barrel 22 may be designed in accordance with the application and various conditions, so as to be set to about 14 mm to 500 mm, or set to about 14 mm to 400 mm, or set to about 14 mm to 200 mm, for example.

Figure 2:
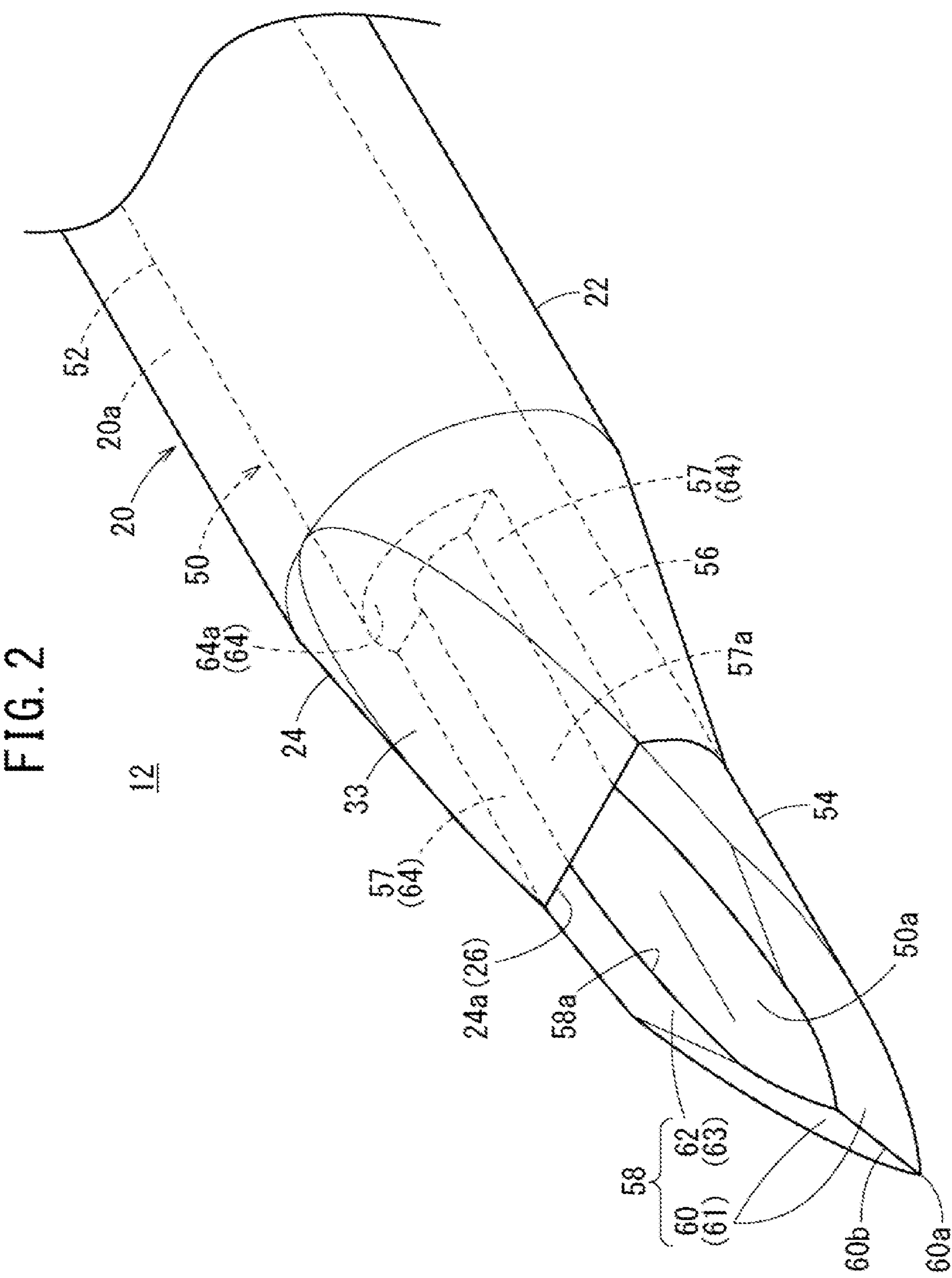
FIG. 2 is an enlarged perspective view illustrating a distal side of a double structure needle of FIG. 1.

As illustrated in FIG. 2, the tapered portion 24 has a tapered shape having an outer diameter gradually decreasing from the proximal end connected to the outer needle side barrel 22 in the distal direction. At the distal most end 24*a* of the tapered portion 24 (catheter 20), a distal end opening 26 communicating with the inner cavity 20*a* is provided. The configuration of the tapered portion 24 also relates to the shape of the inner needle 50, and thus will be described below in detail.

The material from which the catheter 20 is formed is not particularly limited, and soft resin material is suitable. Examples include: fluoride resin such as polytetrafluoroethylene (PTFE), ethylene tetrafluoroethylene copolymer (ETFE), and perfluoroalkoxy fluororesin (PFA); an olefinic resin such as polyethylene and polypropylene or a mixture thereof; and a polyurethane, a polyester, a polyamide, a polyether nylon resin, a mixture of an olefinic resin and an ethylene/vinyl acetate copolymer. The catheter 20 according to the present embodiment is formed of polyurethane having heat shrinkability.

Returning to FIG. 1, the catheter hub 40 is formed in a cylindrical shape that is harder and larger in diameter than the catheter 20 and long in the axial direction. A hollow portion 40*a* communicating with the proximal end opening of the outer needle side barrel 22 is provided inside the catheter hub 40. Although not illustrated, the hollow portion 40*a* may house a hemostatic valve for preventing back flow of blood at the time of puncture with the inner needle 50, a plug for penetrating the hemostatic valve in accordance with insertion of the infusion tube to allow infusion, or the like.

The material from which the catheter hub 40 is formed is not particularly limited, and examples of these include a thermoplastic resin such as polypropylene, polycarbonate, polyamide, polysulfone, polyallylate, and methacrylate-butylene-styrene copolymer.

Meanwhile, the inner needle 50 is a hollow tube having a rigidity capable of puncturing the skin of the living body, and is disposed to penetrate through the inner cavity 20*a* of the catheter 20 and the hollow portion 40*a* of the catheter hub 40, in the assembled state illustrated in FIG. 1. The inner needle 50 includes: an inner needle side barrel 52 (barrel) longer than the entire length of the catheter 20; a needle tip portion 54 extending short at the distal end of the inner needle 50; and a transition portion 56 continuously connecting both sites, namely, the inner needle side barrel 52 and the needle tip portion 54. A needle hole 50*a* is linearly formed through a center axis portion of the inner needle 50.

The inner needle side barrel 52 of the inner needle 50 extends in a tubular shape in the axial direction of the inner needle 50 and has a constant outer diameter and inner diameter along the center axis of the inner needle 50. The proximal end portion of the inner needle side barrel 52 is firmly fixed inside the needle hub 70 with an appropriate fixing method such as fusion bonding, adhesion, and insert molding.

As illustrated in FIG. 2, a tubular body manufactured to have a same diameter as the inner needle side barrel 52 is appropriately cut into the needle tip portion 54 of the inner needle 50 to have the blade surface 58 at a portion in the circumferential direction at the time of manufacture. This blade surface 58 includes a needle tip opening 58*a* communicating with the needle hole 50*a*. The length in the axial direction of the needle tip portion 54 may preferably be 1 mm to 10 mm, for example, depending on the entire length and the outer diameter of the inner needle 50.

Furthermore, in the present embodiment, the blade surface 58 includes four surfaces (a pair of distal end split surfaces 60 and a pair of proximal end inclined surfaces 62). The pair of distal end split surfaces 60 is continuous with a point 60*a* and a ridge portion 60*b* at a distal most end so as to constitute a first site 61 that goes around the needle tip opening 58*a* toward the proximal side to be separated away in a width direction and having gradually increasing mutual widths. The pair of proximal end inclined surfaces 62 are each connected to the proximal ends of the pair of distal end split surfaces 60 so as to form a portion of an arc of a semi-ellipse that goes around the needle tip opening 58*a* in the proximal direction and constitute a second site 63 having gradually decreasing mutual widths. The pair of distal end split surfaces 60 and the pair of proximal end inclined surfaces 62 can be formed by cutting the tubular body three times.

Figure 3:
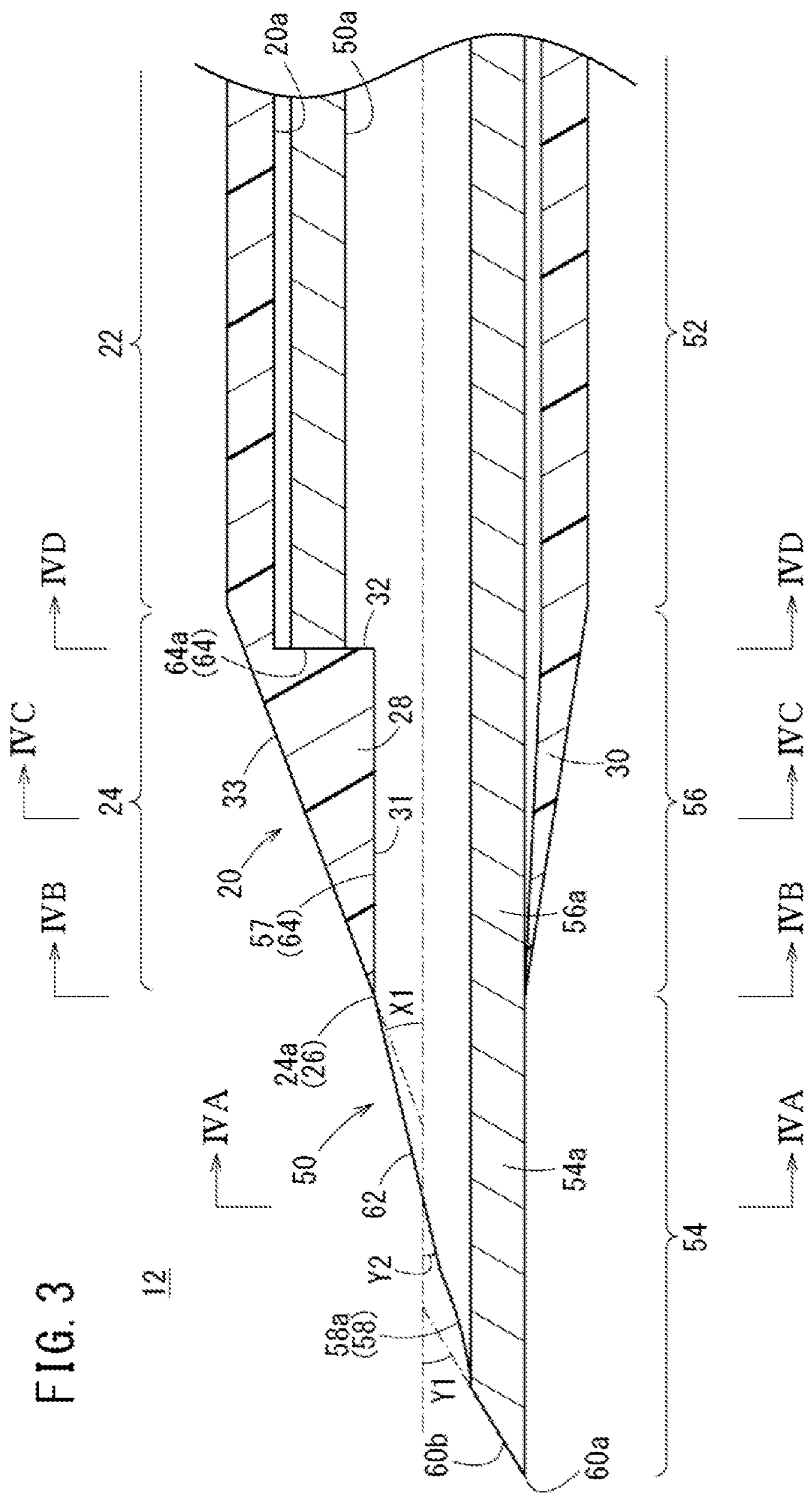
FIG. 3 is a side cross section of the double structure needle of FIG. 2.

The pair of distal end split surfaces 60 (first site 61 of the blade surface 58) are formed in a flat shape, each of which faces outer side in a width direction opposite to each other and is formed to be short in the axial direction in a side cross section in FIG. 3. This pair of distal end split surfaces 60, together with the point 60*a* and the ridge portion 60*b*, constitutes a portion that cuts through the living tissue. An inclination angle Y1 of the ridge portion 60*b* with respect to the center axis of the inner needle 50 is preferably designed to be an angle facilitating insertion of the first site 61, for example, preferably in a range of 15° to 40°.

Figure 4A:
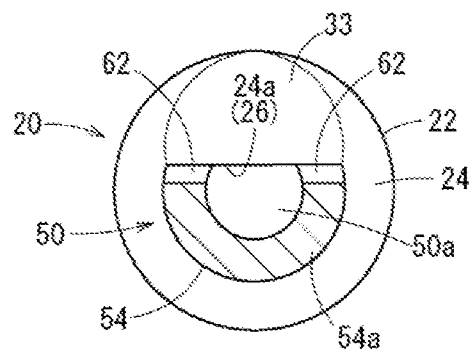
FIG. 4A is a cross section taken along line IVA-IVA of FIG. 3.

Meanwhile, the pair of proximal end inclined surfaces 62 (second site 63 of the blade surfaces 58) are inclined at a same inclination angle with respect to each other in the side cross section illustrated in FIG. 3, and exhibits a flat shape facing the upward direction and the distal direction. Formation portion of the proximal end inclined surface 62 is formed at a C-shaped arcuate wall portion 54*a* having a needle tip opening 58*a* on the upper side in cross section (refer to FIG. 4A) orthogonal to the center axis of the inner needle 50. The arcuate wall portion 54*a* gradually increases in height in the proximal direction on the basis of the inclination of the proximal end inclined surface 62. An inclination angle Y2 of the proximal end inclined surface 62 with respect to the center axis of the inner needle 50 is designed to be the inclination angle Y1 or less ($0° < Y2 \leq Y1$) of the ridge portion 60*b*. The inclination angle Y2 of the pair of proximal end inclined surfaces 62 may preferably be, for example, in the range of 5° to 20°.

Figure 4B:
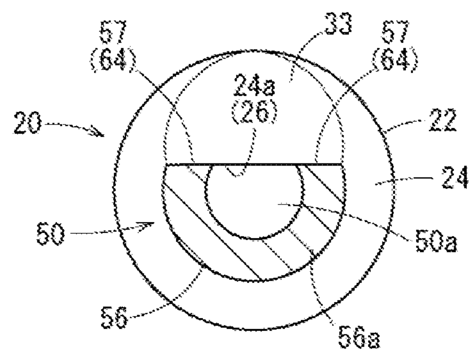
FIG. 4B is a cross section taken along line IVB-IVB of FIG. 3.
Figure 4C:
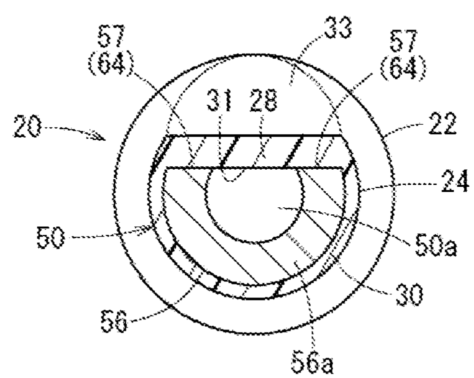
FIG. 4C is a cross section taken along line IVC-IVC of FIG. 3.

As illustrated in FIGS. 2 and 3, the transition portion 56 of the inner needle 50 is a site that bridges between the tubular inner needle side barrel 52 and the needle tip portion 54 having the blade surface 58. This transition portion 56 is formed at a C-shaped arcuate wall portion 56*a* that is open at an upper portion of the needle hole 50*a* and joined to the arcuate wall portion 54*a* in cross section (refer to FIGS. 4B and 4C) orthogonal to the center axis of the inner needle 50. A semicircular needle hole 50*a* communicating with an upper opening port 57*a* extends on the center axis of the transition portion 56. Moreover, the outer peripheral surface and the inner peripheral surface of the arcuate wall portion 56*a* are flush with the outer peripheral surface and the inner peripheral surface of the inner needle side barrel 52 and the needle tip portion 54, along the axial direction.

A pair of extending surfaces 57 (both end surfaces of the arcuate wall portion 56*a*: intermediate surface) is provided on an upper surface of the transition portion 56 across the opening port 57*a* in the width direction. Each extending surface 57 is formed in a flat shape extending parallel to the center axis of the inner needle 50. That is, the inner needle 50 has a height of the arcuate wall portion 54*a* having a C-shaped cross section gradually increasing in the proximal direction in a formation range of the needle tip portion 54, while having a height of the arcuate wall portion 56*a* having a C-shaped cross section extending constantly in the proximal direction in a formation range of the transition portion 56. In other words, the transition portion 56 has a recess 64 that is cut out (recessed) inward in the radial direction, on the blade surface 58 side of the needle tip portion 54. The presence of the recess 64 provides the transition portion 56 with a pair of extending surfaces 57 and a locking surface 64*a* to be described below, while providing the transition portion 56 with a half-pipe shape in which a vertical dimension regarding the center axis is shorter than the inner needle side barrel 52 (recessed inward in the radial direction from the outer peripheral surface of the inner needle side barrel 52).

The pair of extending surfaces 57 is located somewhat above the center axis of the inner needle 50 (inner needle side barrel 52) in side cross section. With this configuration, it is possible to satisfactorily achieve communicability of the needle hole 50*a* in the axial direction. The length in the axial direction of the transition portion 56 may preferably be 0.5 mm to 8 mm, for example, depending on the entire length and the outer diameter of the inner needle 50.

Figure 4D:
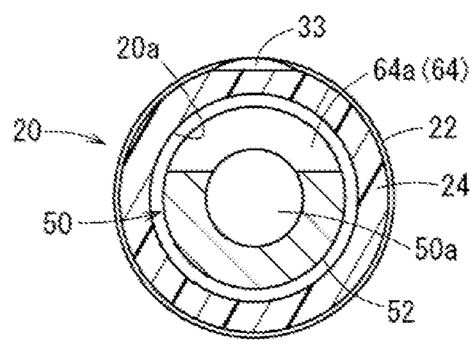
FIG. 4D is a cross section taken along line IVD-IVD of FIG. 3.

A boundary between the transition portion 56 and the inner needle side barrel 52 includes the locking surface 64*a* (inner needle side locking surface) formed to protrude upward (in the vertical direction) from the proximal ends of the pair of extending surfaces 57 to restrict the retraction of the catheter 20 with respect to the inner needle 50. As illustrated in FIG. 4D, this locking surface 64*a* has an arcuate shape in cross section corresponding to the tubular shape of the inner needle side barrel 52 and faces the distal direction of the inner needle 50.

The material to form the inner needle 50 is not particularly limited, and examples include metal materials such as stainless steel, aluminum or aluminum alloy, titanium or titanium alloy, hard resin, and ceramics. Note that the inner needle 50 may include a groove portion obtained by partially cutting the outer peripheral surface in the axial direction, or may include a lateral hole communicating with the needle hole 50*a*. In addition, the inner needle 50 may be a solid needle.

Returning to FIG. 1, the needle hub 70 is formed as a case by which the double structure needle 12 is operable on the proximal side, and fixedly holds the inner needle 50 inside this case. The needle hub 70 is formed in an elongated shape easily grasped with one hand while accommodating and connecting with the proximal side of the catheter hub 40. Configurations of the catheter hub 40 and the needle hub 70 of the catheter assembly 10 are not limited to the above-described configuration, and various configurations may be adopted.

Next, the double structure needle 12 in a state (assembled state) where the above configuration is assembled to enable puncture to a patient will be described in detail. As described above, in the catheter assembly 10, the inner needle 50 is inserted through the inner cavity 20*a* of the catheter 20, with a center axis of the catheter 20 and the inner needle 50 coaxially arranged in the assembled state. The needle tip portion 54 at the distal end of the inner needle 50 is exposed from the distal end (distal most end 24*a*) of the catheter 20.

In the present embodiment, the tapered portion 24 of the catheter 20 covers the entire transition portion 56 of the inner needle 50, as illustrated in FIGS. 2, 3, and 4B to 4D. Specifically, the tapered portion 24 extends from a position overlapping the distal end of the inner needle side barrel 52 to the boundary between the needle tip portion 54 (proximal end inclined surface 62) of the inner needle 50 and the transition portion 56. This configuration reduces the amount of protrusion of the inner needle 50 protruding from the distal end of the catheter 20. Furthermore, the distal most end 24*a* of the tapered portion 24 is positioned at the proximal end of the blade surface 58, with substantially no step with the outer peripheral surface of the needle tip portion 54.

On the inner surface (inner peripheral portion) of the tapered portion 24, an inner bulging portion 28 protruding inward in the radial direction is provided at a position having phase matching with the pair of extending surfaces 57 among the circumferential position surrounding the transition portion 56. The inner bulging portion 28 is formed so as to fill the recessed portion 64 of the transition portion 56, with a gradual increase in its wall thickness at a great increase rate, starting from the distal most end in the proximal direction as viewed in side cross section. In contrast, the circumferential positions of the tapered portion 24 other than the inner bulging portion 28 are formed as an arcuate portion 30 gradually increasing at a small increase rate, starting from the distal most end in the proximal direction.

Specifically, the inner bulging portion 28 is formed in a right-angled triangle shape in side cross section, and includes: a first opposing surface 31 opposite to the pair of extending surfaces 57 of the transition portion 56; and a second opposing surface 32 (catheter side locking surface) opposite to the locking surface 64*a* of the inner needle 50. The first opposing surface 31 is formed as a flat surface parallel to the center axis of the catheter 20 (outer needle side barrel portion 22), while the second opposing surface 32 is formed as a flat surface orthogonal to the center axis of the catheter 20.

In the assembled state of the catheter assembly 10, the first opposing surface 31 of the tapered portion 24 comes in contact with the pair of extending surfaces 57 of the transition portion 56, while the second opposing surface 32 of the tapered portion 24 comes in contact with the locking surface 64*a* of the inner needle 50. The second opposing surface 32 of the inner bulging portion 28 is caught on the locking surface 64*a* of the tapered portion 24, thereby suppressing relative movement of the catheter 20 in the proximal direction with respect to the inner needle 50 even when shrinkage occurs in the catheter 20.

Furthermore, the tapered portion 24 has an outer flat surface 33 on the outer peripheral surface of the formation portion of the inner bulging portion 28. The outer flat surface 33 is formed in a semi-elliptical shape that is substantially symmetrical with the proximal end inclined surface 62 of the inner needle 50 and is inclined at a predetermined inclination angle X1. The inclination angle X1 of the outer flat surface 33 with respect to the center axis of the catheter 20 is preferably somewhat larger than the inclination angle Y2 of the proximal end inclined surface 62 of the inner needle 50. This allows an angle between the outer flat surface 33 and the blade surface 58 (proximal end inclined surface 62) to be an obtuse angle to a sufficient degree. Note that the inclination angle X1 of the outer flat surface 33 may be set smaller than the inclination angle Y2 or may be set to be equal to the inclination angle Y2 depending on the strength and length required for the tapered portion 24.

Still further, the catheter 20 is formed of a material containing polyurethane, making it possible to facilitate shaping of the tapered portion 24 of the catheter 20. That is, in the manufacture of the catheter 20, the catheter 20 is pressed against a heated mold and processed into a desired shape. Thereafter, the catheter 20 is covered with a tubular material and heated to be formed into a shape that conforms to the shape of the inner needle 50 or the shape of the transition portion 56 (pair of extending surfaces 57 and locking surface 64*a*) of the inner needle 50. This processing causes heat shrinkage in the catheter 20, making it possible to form the tapered portion 24 into a desired shape (shape enabling the second opposing surface 32 and the locking surface 64*a* to be further reliably brought into contact with each other). The processing of the tapered portion 24 is not limited to the above-described method, and any method by which the tapered portion 24 can be processed into a desired shape may be used, such as heat melting, heating deformation, and machine cutting. Furthermore, the tapered portion 24 may be finally molded by only heat melting or the like, or may be molded by only covering a tubular material to use thermal shrinkage.

The catheter assembly 10 according to the present embodiment is essentially configured as described above, and its function and effect will be described below.

As illustrated in FIGS. 2 to 4D, the inner bulging portion 28 of the catheter 20 is disposed in the transition portion 56 (recess 64) of the inner needle 50, and then, the catheter assembly 10 is provided to the user as a product in this assembled state. In this assembled state, the first opposing surface 31 of the catheter 20 is in contact with the pair of extending surfaces 57 of the inner needle 50, while the second opposing surface 32 is in contact with the locking surface 64*a* of the inner needle 50.

Here, it is assumed that shrinkage occurs in the catheter 20 while the catheter assembly 10 is stored. In this case, the outer needle side barrel 22 constituting the major part of the catheter 20 shrinks, applying a force to the tapered portion 24 of the catheter 20 from the outer needle side barrel 22 in the proximal direction relative to the inner needle 50. Fortunately, however, the catheter assembly 10 according to the present embodiment has a configuration in which the second opposing surface 32 of the tapered portion 24 (inner bulging portion 28) is in contact with the locking surface 64*a*, which is a distal end surface of the inner needle side barrel 52. That is, the inner bulging portion 28 is caught at the distal end of the inner needle 50, restricting the movement of the tapered portion 24 in the proximal direction. Accordingly, even when shrinkage occurs in the catheter 20, the tapered portion 24 maintains arrangement positions in the assembled state, with no change in the amount of protrusion of the needle tip portion 54 of the inner needle 50 protruding from the distal most end 24*a* of the tapered portion 24.

The catheter assembly 10 is used, for example, in construction of an introduction part for infusion into a patient. In use of the catheter assembly 10, a user grasps and operates the needle hub 70 and punctures the patient with the double structure needle 12. At this time, the first site 61 exposed from the distal end of the catheter 20 cuts through the living tissue (skin, subcutaneous tissue, blood vessel wall, or the like) so as to insert the needle tip portion 54 into a blood vessel.

Further, with advancement of the double structure needle 12, the proximal end inclined surface 62 (second site 63) is next inserted into the living tissue, and then, the catheter 20 is also inserted into the living tissue. As described above, since the distal most end 24*a* of the tapered portion 24 is in contact with the outer peripheral surface of the needle tip portion 54, suppressing occurrence of a step between the inner needle 50 and the catheter 20. In addition, the proximal end inclined surface 62 and the outer flat surface 33 are continuously connected at a large obtuse angle. This suppresses the resistance applied from the living tissue to the catheter 20, leading to smooth insertion of the tapered portion 24 into the blood vessel wall. In particular, with the first opposing surface 31 of the tapered portion 24 being caught with the locking surface 64*a* of the inner needle 50, it is possible to suppress misalignment of the catheter 20 even when a force to retract the catheter 20 is applied at insertion of the catheter 20.

In addition, the catheter assembly 10 has a configuration in which the amount of protrusion of the needle tip portion 54 protruding from the distal end of the catheter 20 is small, making it possible to suppress an arrival of the needle tip portion 54 to an opposite side of the blood vessel inner wall and damage caused by this at a stage when the tapered portion 24 is inserted into the blood vessel wall. As a result, the catheter 20 is advanced relative to the inner needle 50 after the catheter 20 is inserted into the blood vessel, enabling smooth insertion of the catheter 20 into the blood vessel.

After insertion of the catheter 20, the inner needle 50 is retracted relative to the catheter 20 in the proximal direction, so as to extract the inner needle 50 from the catheter 20. At this time, the inner surface of the catheter 20 includes no portion that restricts the retraction of the inner needle 50, facilitating retraction of the inner needle 50. Furthermore, the first opposing surface 31 and the pair of extending surfaces 57 are in contact with each other in parallel in the axial direction at retraction of the inner needle 50. This also enables guiding the inner needle 50 smoothly in the proximal direction alone.

As described above, the catheter assembly 10 according to the present embodiment has a simple configuration in which the locking surface 64*a* and the second opposing surface 32 are in contact with each other, making it possible to suppress the retraction of the distal end of the catheter 20. That is, the second opposing surface 32 is caught on the locking surface 64*a* in the assembled state, leading to a state in which the relative movement of the catheter 20 in the proximal direction with respect to the inner needle 50 is constantly restricted. With this configuration, it is possible to maintain the amount of protrusion of the inner needle 50 protruding from the catheter 20 even with occurrence of shrinkage in the catheter 20, enabling satisfactory insertion of the catheter 20 into the living body.

In this case, with a configuration in which the transition portion 56 has the pair of extending surfaces 57 and the locking surface 64*a*, with the locking surface 64*a* being orthogonal to the center axis of the inner needle 50, it is possible to set the catheter 20 to be firmly caught on the locking surface 64*a*. At this time, the inner bulging portion 28 of the catheter 20 has the second opposing surface 32 orthogonal to the center axis of the catheter 20, with the catheter 20 caught on the locking surface 64*a* of the inner needle 50, leading to further reliable restriction of the relative movement of the catheter 20 in the proximal direction. Furthermore, the tapered portion 24 of the catheter 20 covers the proximal end of the blade surface 58 in the assembled state, making it possible to further reduce the amount of protrusion of the inner needle 50 without losing the puncture function of the blade surface 58.

Note that the catheter assembly 10 is not limited to the above-described configuration, and various configurations may be adopted. For example, even with the catheter assembly 10 not including the tapered portion 24 on the distal side and including the inner bulging portion 28 provided inside an extending linear tube, it is still possible to restrict relative retraction of the tapered portion 24 with respect to the inner needle 50.

Several modifications of the catheter assembly 10 will be described below. In the following description, the same reference numerals are given to components having the same configuration or the same functions as those of the catheter assembly 10 according to the embodiment described above, and a detailed description thereof will be omitted.

Figure 5:
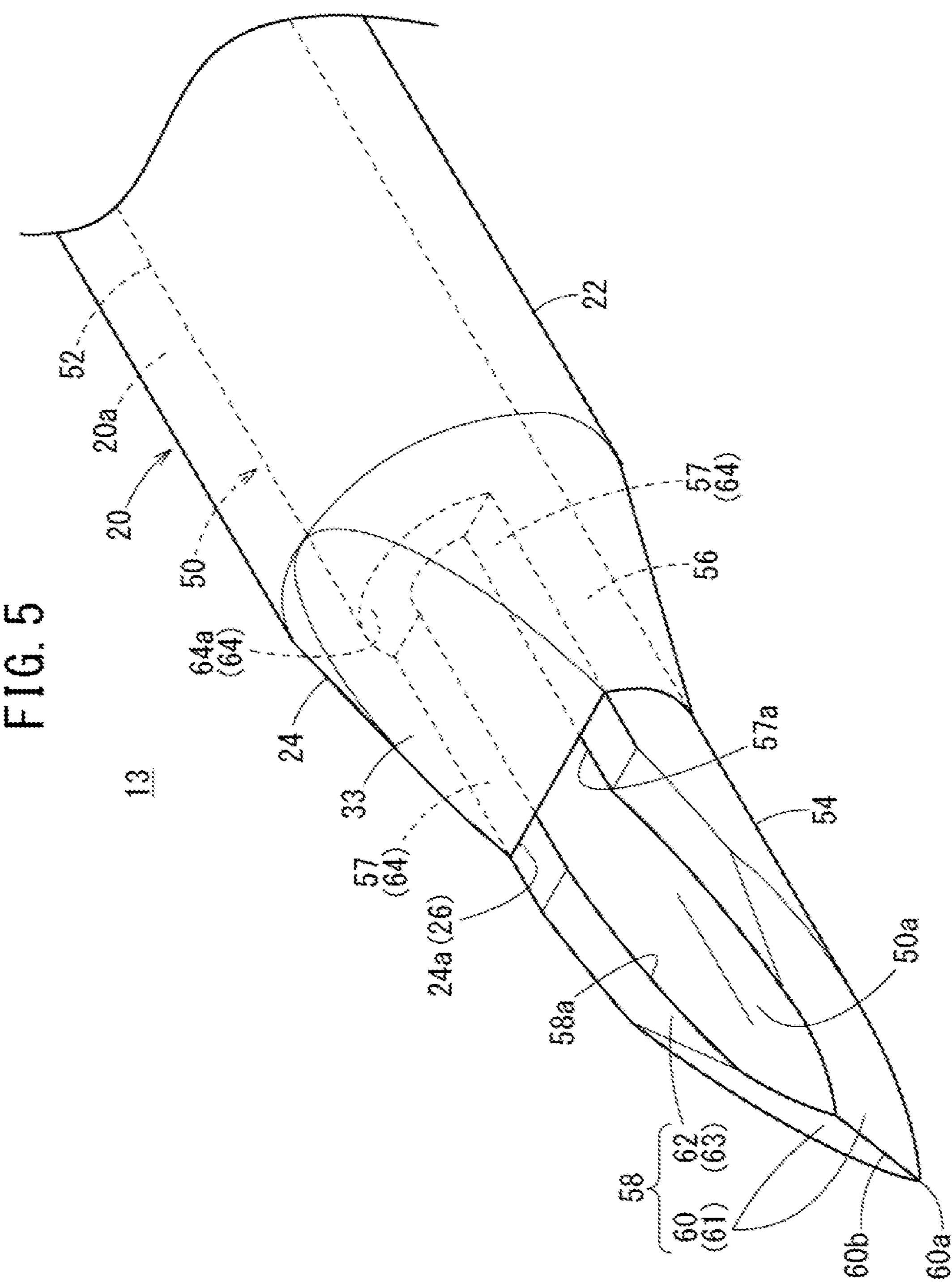
FIG. 5 is an enlarged perspective view illustrating a distal side of a double structure needle according to a first modification.

As illustrated in FIG. 5, a double structure needle 13 according to a first modification differs from the above-described double structure needle 12 in that the tapered portion 24 of the catheter 20 exposes the extending surface 57 on the distal side of the transition portion 56 together with the needle tip portion 54. Even with the catheter assembly 10 in which the distal most end 24*a* of the tapered portion 24 is located away from the proximal end of the blade surface 58 in this manner, it is still possible to form the inner bulging portion 28 in the catheter 20 in accordance with the transition portion 56 (recess 64). In addition, similarly to the double structure needle 12 according to the present embodiment, the inner bulging portion 28 easily brings the second opposing surface 32 (refer to FIG. 3) into contact with the locking surface 64*a* of the inner needle 50.

Figure 6:
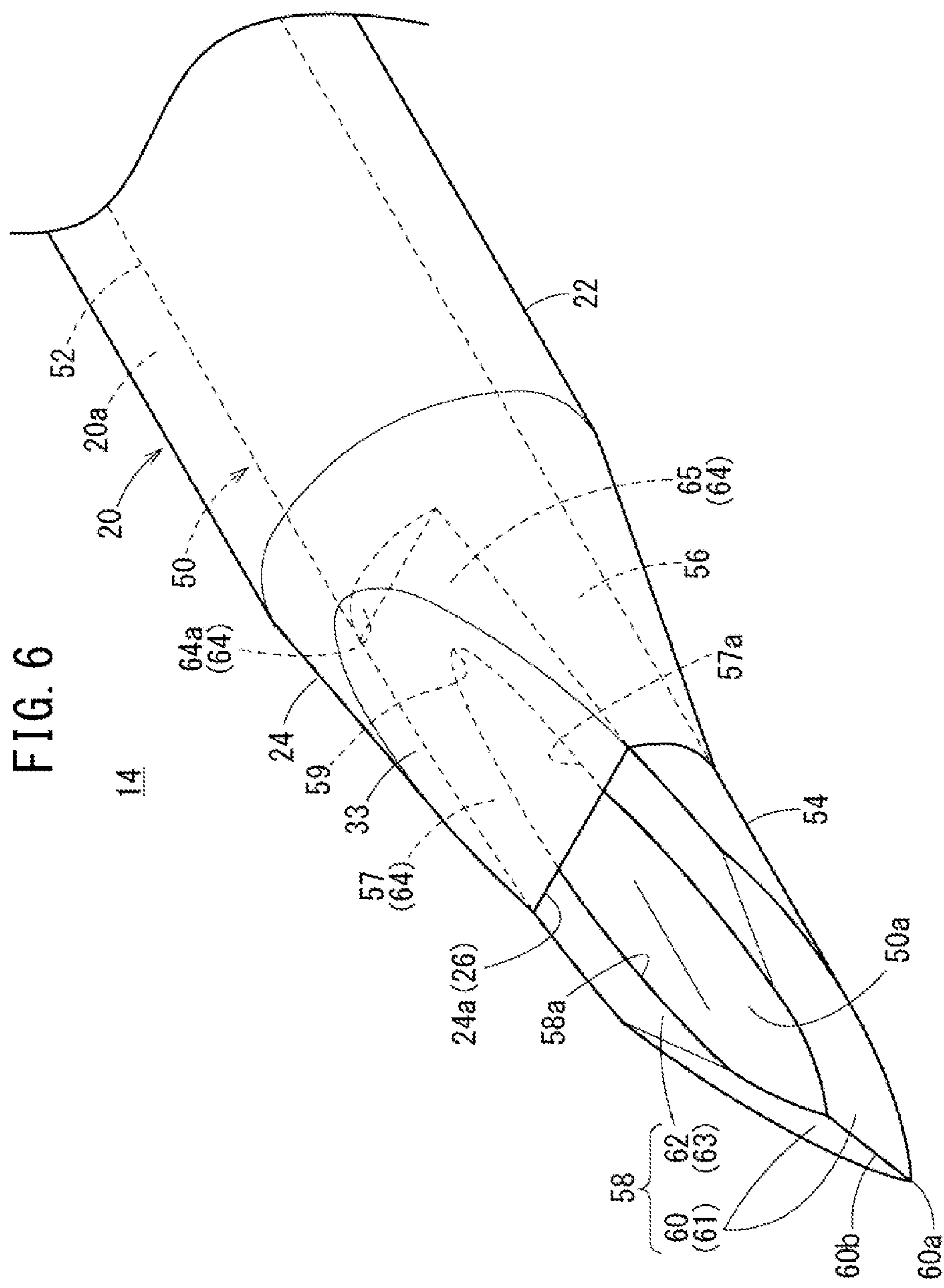
FIG. 6 is an enlarged perspective view illustrating a distal side of a double structure needle according to a second modification.
Figure 7:
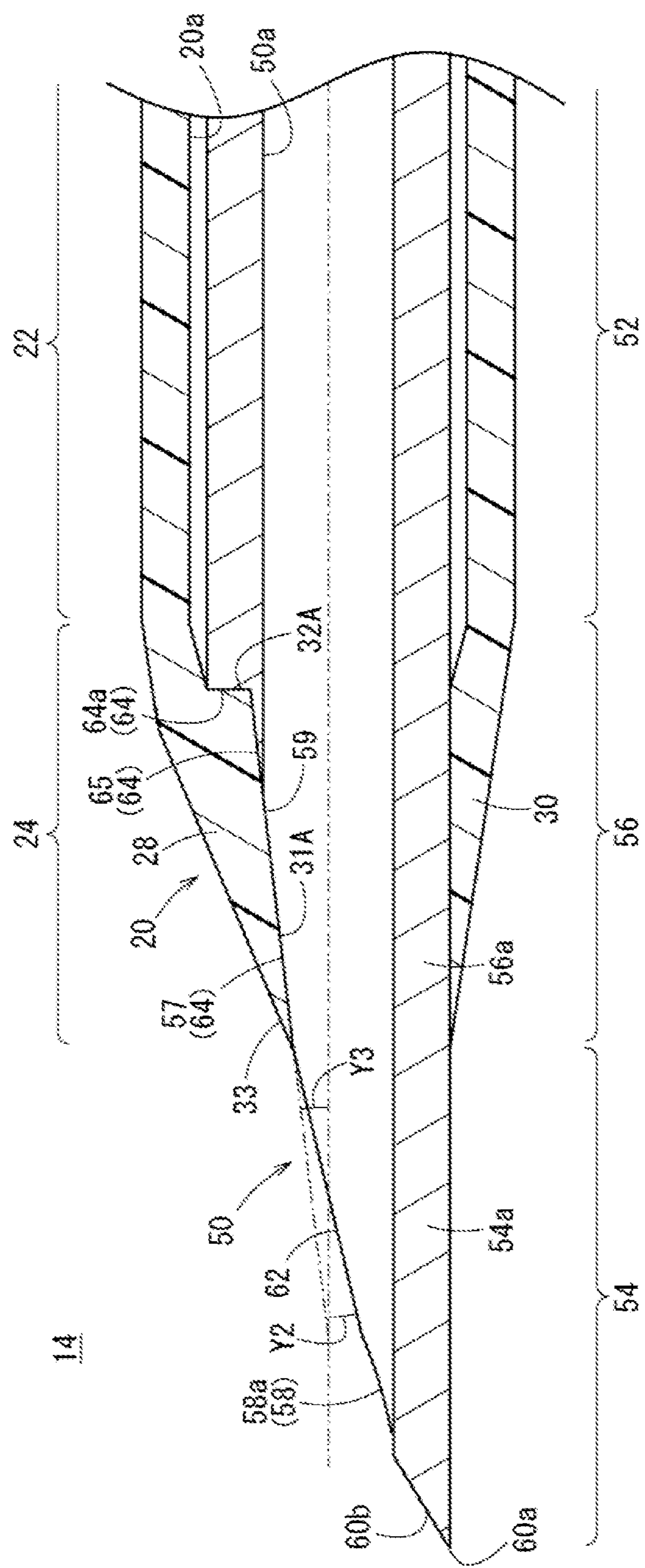
FIG. 7 is a side cross section of the double structure needle in FIG. 6.

As illustrated in FIGS. 6 and 7, a double structure needle 14 according to a second modification differs from the above-described double structure needles 12 or 13 in that an upper surface of the transition portion 56 of the inner needle 50 is not parallel to the center axis of the inner needle 50, and that the first opposing surface 31 of the catheter 20 is also nonparallel.

Specifically, while the transition portion 56 includes the recess 64 cut out inward in the radial direction with respect to the inner needle side barrel 52, the transition portion 56 is formed as an upper surface (intermediate surface) gently inclined diagonally upward in the proximal direction of the inner needle 50. Accordingly, the upper surface of the transition portion 56 is formed with the pair of extending surfaces 57 and a proximal end joining surface 65 that is flush with the proximal side of the pair of extending surfaces 57 and is inclined at the same inclination angle as the pair of extending surfaces 57, and in addition, an inclination angle Y3 of the upper surface with respect to the center axis of the inner needle 50 is smaller than the inclination angle Y2 of the proximal end inclined surface 62 (blade surface 58). The proximal end joining surface 65 closes the upper part of the needle hole 50*a* to form a rim 59 of the needle tip opening 58*a*. In addition, a step is formed at a boundary between the transition portion 56 and the inner needle side barrel 52, and the distal end surface of the inner needle side barrel 52 forms the locking surface 64*a* orthogonal to the center axis of the inner needle 50.

In contrast, the first opposing surface 31A of the tapered portion 24 (inner bulging portion 28) matches the pair of extending surfaces 57, the needle tip opening 58*a*, and the proximal end joining surface 65, and is formed to be inclined at the same inclination angle. Due to the inclination of the first opposing surface 31A, a second opposing surface 32A of the tapered portion 24 is formed to be short in the radial direction at an angle orthogonal to the center axis of the inner needle 50.

The double structure needle 14 according to the second modification is basically configured as described above. With this double structure needle 14, it is also possible to achieve effect similar to the cases of the above-described double structure needles 12 and 13. That is, the second opposing surface 32A of the catheter 20 is caught on the locking surface 64*a* of the inner needle 50, the movement of the tapered portion 24 in the proximal direction is restricted even when shrinkage occurs in the catheter 20. This makes it possible to satisfactorily puncture the blood vessel with the double structure needle 14.

Figure 8:
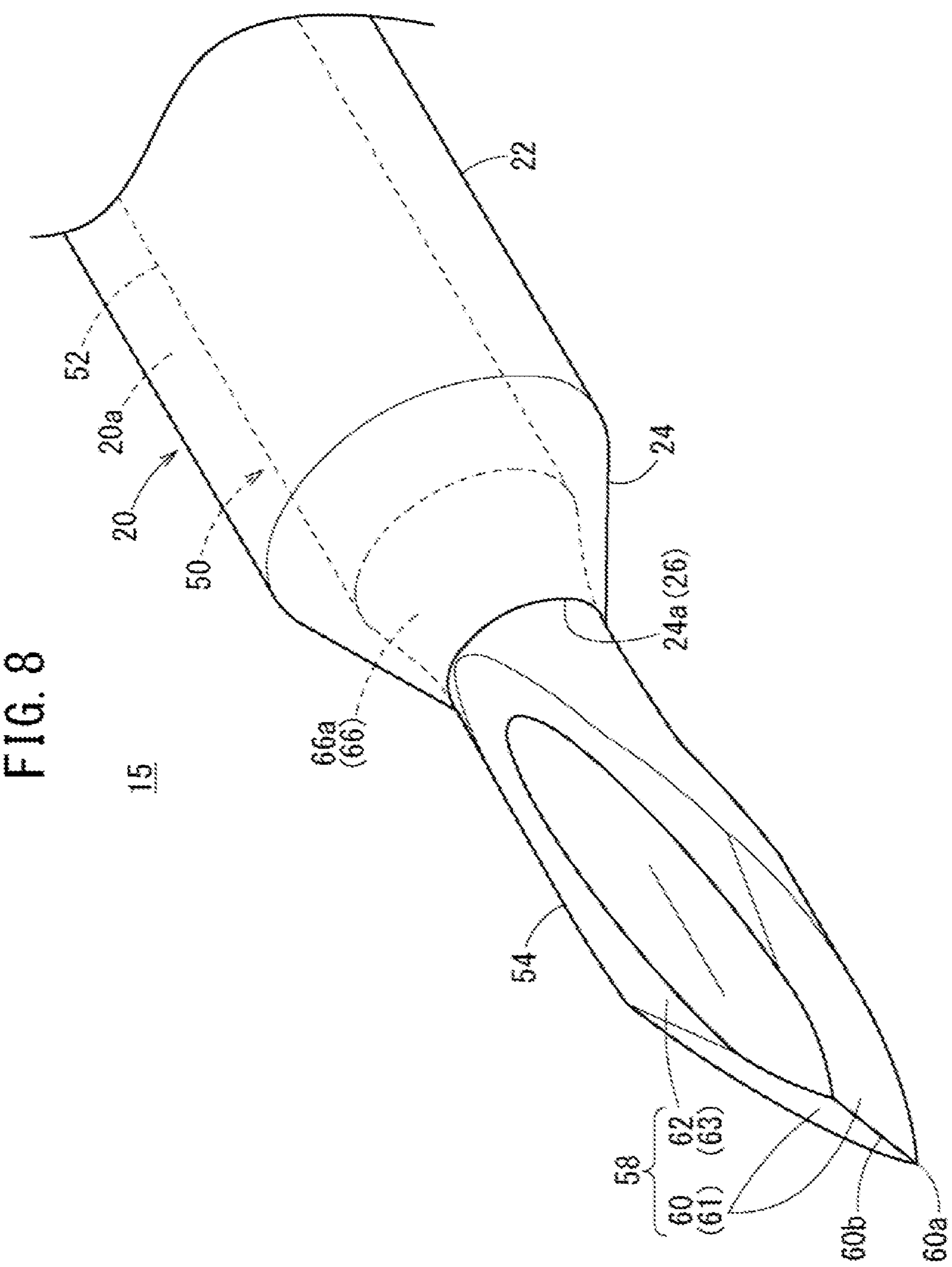
FIG. 8 is an enlarged perspective view illustrating a distal side of a double structure needle according to a third modification.
Figure 9:
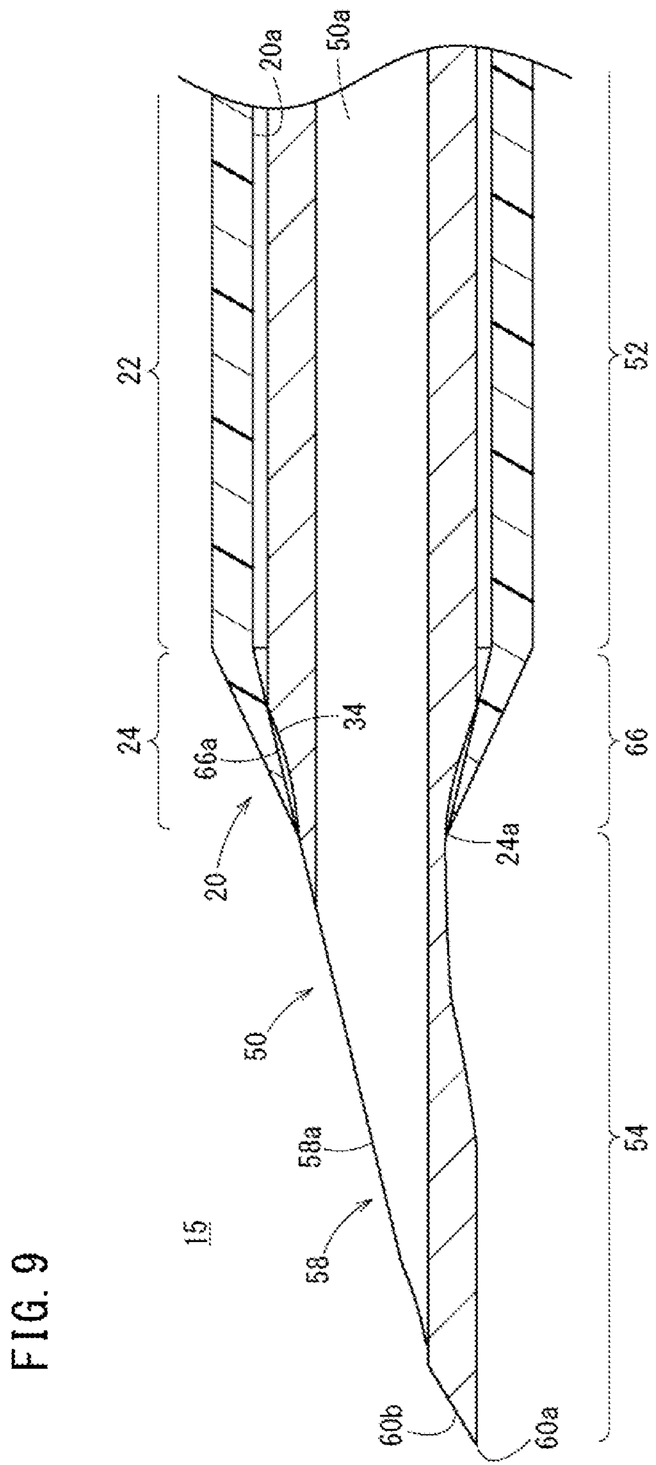
FIG. 9 is a side cross section of the double structure needle in FIG. 8.

As illustrated in FIGS. 8 and 9, a double structure needle 15 according to a third modification differs from the above-described double structure needles 12 to 14 in that it includes a tapered transition portion 66 provided between the inner needle side barrel 52 and the needle tip portion 54 and that the tapered portion 24 of the catheter 20 covers this transition portion 66. As described above, even with a shape having no cut out portion in the transition portion 66 of the inner needle 50 and having a tapered recess that is recessed inward in the radial direction, it is still possible to restrict retraction of the tapered portion 24 of the catheter 20.

Specifically, an outer peripheral surface of the transition portion 66 includes a conical surface 66*a* inclined at a predetermined angle with respect to the center axis of the inner needle 50 in a side cross section, having an outer diameter gradually reducing from the distal end of the inner needle side barrel 52 toward the proximal end of the needle tip portion 54. The transition portion 66 having the conical surface 66*a* reduces the entire outer diameter of the inner needle 50 to shorten the length of the needle tip portion 54 in the axial direction (formation range of the blade surface 58). Therefore, the amount of protrusion of the inner needle 50 can be reduced simply by covering the transition portion 66 with the tapered portion 24 of the catheter 20 in the assembled state. Meanwhile, in order to form a cut that enables smooth insertion of the catheter 20, the blade surface 58 is preferably formed to spread outward in the width direction (or vertical direction) from the distal end of the transition portion 66 toward the distal direction.

Meanwhile, an inner surface of the tapered portion 24 of the catheter 20 is formed as a tapered inner surface 34 (catheter side locking surface) that is inclined along the conical surface 66*a* of the inner needle 50. The inner diameter of the tapered inner surface 34 is reduced together with the outer peripheral surface, in the distal direction. The tapered portion 24 comes in contact with the proximal end of the conical surface 66*a* of the inner needle 50. At the same time, the distal most end 24*a* of the tapered portion 24 is positioned at a boundary between the transition portion 66 and the needle tip portion 54 of the inner needle 50 and is in contact with the outer peripheral surface of the inner needle 50.

The minimum inner diameter of the tapered inner surface 34 (catheter side locking surface) of the distal most end 24*a* of the tapered portion 24 is smaller than the maximum outer diameter of the conical surface 66*a* (inner needle side locking surface). This configuration allows the tapered inner surface 34 of the catheter 20 to be caught on the conical surface 66*a* of the inner needle 50, so as to restrict the movement of the tapered portion 24 in the proximal direction when shrinkage occurs in the catheter 20.

In this case, the tapered portion 24 of the catheter 20 can be formed in a shape having a wall thickness gradually decreasing in the distal direction without having the inner bulging portion 28 and the outer flat surface 33, making it possible to facilitate molding of the catheter 20. The distal most end 24*a* of the tapered portion 24 may be in contact with a midway position of the transition portion 66 (on the conical surface 66*a* of the transition portion 66) as well as being in contact with the boundary between the needle tip portion 54 and the transition portion 66, and even a configuration to cover up to the proximal side of the blade surface 58 of the inner needle 50 would be allowable.

As described above, even with the double structure needle 15 according to the third modification, it is possible to achieve effects similar to the cases of the above-described double structure needles 12 to 14. That is, the tapered inner surface 34 of the catheter 20 comes in contact with the conical surface 66*a* of the inner needle 50, making it possible to restrict movement of the tapered portion 24 in the proximal direction even when shrinkage occurs in the catheter 20. This makes it possible to satisfactorily puncture the blood vessel with the double structure needle 15.

Note that the inner needle 50 may have a configuration in which the blade surface 58 (proximal end inclined surface 62) extends to the locking surface 64*a* without having the transition portion 66. In this case, the catheter 20 may have a configuration in which the inner surface (catheter side locking surface) of the catheter 20 comes in contact with the locking surface 64*a* while covering the proximal side of the blade surface 58.

Figure 10A:
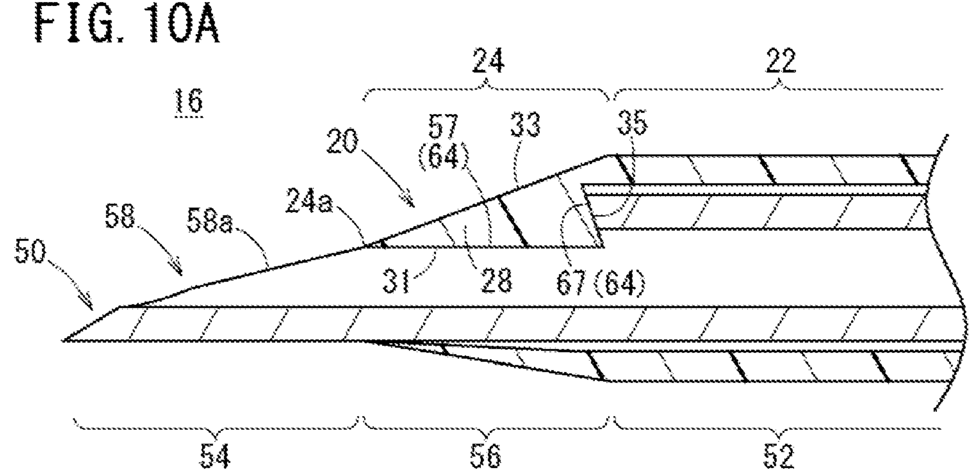
FIG. 10A is a side cross section of a double structure needle according to a fourth modification.

In addition, there are various other modifications of an engaged state of the catheter 20 and the inner needle 50. For example, a double structure needle 16 according to a fourth modification illustrated in FIG. 10A differs from the above-described double structure needles 12 to 15 in that a locking surface 67 of the inner needle 50 is inclined in the proximal direction inward in the radial direction so as to intersect with the center axis of the inner needle 50 non-orthogonally. In this case, with a configuration in which the inner bulging portion 28 of the tapered portion 24 allows the second opposing surface 35 to be inclined inward in the radial direction in the proximal direction to match the inclination of the locking surface 67, it would be possible to more firmly lock the tapered portion 24.

Figure 10B:
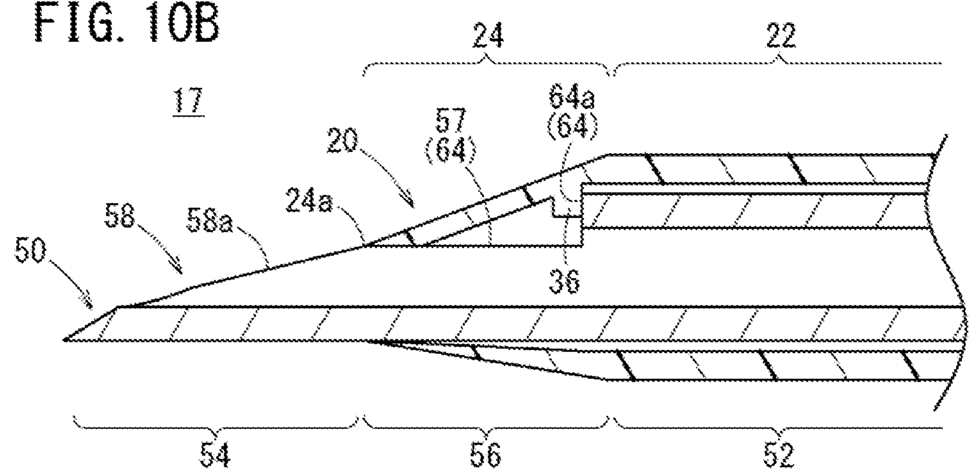
FIG. 10B is a side cross section of a double structure needle according to a fifth modification.
Figure 10C:
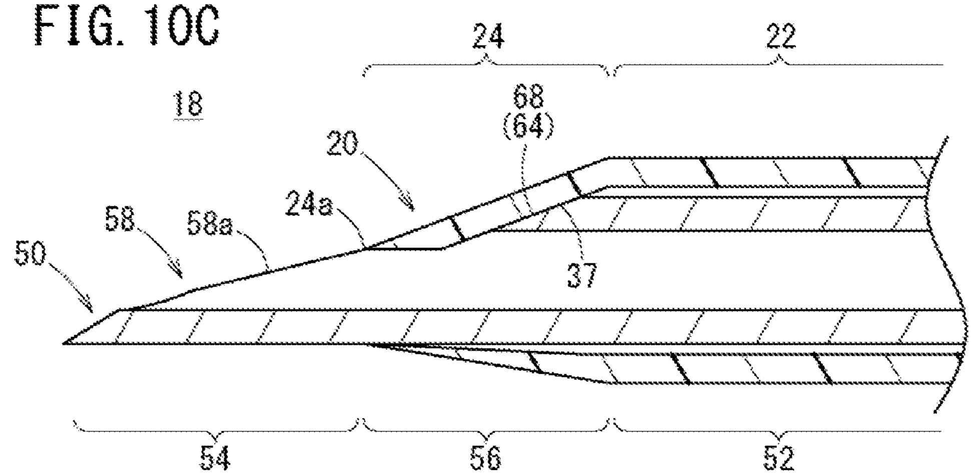
FIG. 10C is a side cross section of a double structure needle according to a sixth modification.

Furthermore, for example, a double structure needle 17 according to a fifth modification illustrated in FIG. 10B differs from the above-described double structure needles 12 to 16 in that the tapered portion 24 does not include the inner bulging portion 28 and that the tapered portion 24 includes a locking protrusion 36 protruding inward in the radial direction. Even with this double structure needle 17 in which the locking protrusion 36 is in contact with the locking surface 64*a* in the assembled state, it is also possible to easily restrict the movement of the tapered portion 24 in the proximal direction Alternatively, a double structure needle 18 according to a sixth modification illustrated in FIG. 10C differs from the above-described double structure needles 12 to 17 in that a locking surface 68 of the inner needle 50 is inclined in the distal direction inward in the radial direction so as to intersect with the center axis of the inner needle 50 non-orthogonally. In this case, with a configuration in which the inner surface 37 of the tapered portion 24 is inclined inward in the radial direction in the distal direction to match the inclination of the locking surface 68, it would be possible to achieve surface contact of the inner surface 37 with the locking surface 68. Accordingly, it is possible to restrict the movement of the tapered portion 24 in the proximal direction.

The present invention is not limited to the above-described embodiments, and various modifications are possible without departing from the scope and spirit of the present invention.

What is claimed is:

1. A catheter assembly comprising:
a catheter having an inner cavity; and
an inner needle retractably located in the inner cavity of the catheter;
wherein the inner needle comprises:
a barrel,
a blade surface located distal of the barrel and being inclined with respect to a center axis of the inner needle, and
an inner needle side locking surface located at least at a portion of an outer surface linking the barrel with the blade surface,
wherein an inner surface of the catheter comprises a catheter side locking surface in contact with the inner needle side locking surface such that relative movement of the catheter in a proximal direction with respect to the inner needle is restricted.

2. The catheter assembly according to claim 1,
wherein the inner needle comprises an intermediate surface located between the inner needle side locking surface and the blade surface, and
wherein the inner needle side locking surface and the intermediate surface form a recess that is recessed inward in a radial direction with respect to the barrel.

3. The catheter assembly according to claim 2,
wherein each of the inner needle side locking surface and the catheter side locking surface is orthogonal to the center axis of the inner needle.

4. The catheter assembly according to claim 2,
wherein the intermediate surface is parallel to the center axis of the inner needle.

5. The catheter assembly according to claim 1,
wherein an inner peripheral portion of the catheter includes a bulging portion protruding inward in a radial direction, and
wherein the catheter side locking surface is a surface of the bulging portion.

6. The catheter assembly according to claim 1,
wherein the inner needle side locking surface extends in a ring shape around the center axis of the inner needle, with an outer diameter of the inner needle side locking surface decreasing in a distal direction,
an inner diameter of the catheter side locking surface decreases in the distal direction, and
a minimum inner diameter of the catheter side locking surface is smaller than a maximum outer diameter of the inner needle side locking surface.

7. The catheter assembly according to claim 1,
wherein a distal most end of the catheter is positioned at a proximal end of the blade surface.

8. The catheter assembly according to claim 1,
wherein the catheter is formed of a material comprising polyurethane.

9. A catheter assembly comprising:
a catheter having an inner cavity; and
an inner needle retractably located in the inner cavity of the catheter;
wherein the inner needle comprises:
a barrel having an outer surface,
a pair of extending surfaces extending distally from the barrel,
an inner needle side locking surface extending from the outer surface of the barrel to the pair of extending surfaces, in a direction traverse to a center axis of the inner needle, and
a blade surface located distal of the barrel, and
wherein an inner surface of the catheter comprises a catheter side locking surface extending in a direction traverse to the center axis of the inner needle, the catheter side locking surface being in contact with the inner needle side locking surface.

10. The catheter assembly according to claim 9, wherein the blade surface comprises:

a pair of proximal end inclined surfaces extending distally from the pair of extending surfaces, and a pair of distal end split surfaces extending distally from the pair of proximal end inclined surfaces to a point of the inner needle.

11. The catheter assembly according to claim 9, wherein each of the inner needle side locking surface and the catheter side locking surface is orthogonal to the center axis of the inner needle.

12. The catheter assembly according to claim 9, wherein the inner needle comprises an intermediate surface located between the inner needle side locking surface and the blade surface, and wherein the inner needle side locking surface and the intermediate surface form a recess that is recessed inward in a radial direction with respect to the barrel.

13. The catheter assembly according to claim 9, wherein an inner peripheral portion of the catheter includes a bulging portion protruding inward in a radial direction, and wherein the catheter side locking surface is a surface of the bulging portion.

14. The catheter assembly according to claim 9, wherein a distal most end of the catheter is positioned at a proximal end of the blade surface.

15. The catheter assembly according to claim 9, wherein a distal most end of the catheter is positioned proximal of a proximal end of the blade surface, such that portions of the pair of extending surfaces are exposed from the catheter.

16. A catheter assembly comprising:

a catheter having an inner cavity; and an inner needle retractably located in the inner cavity of the catheter;

wherein the inner needle comprises:

a barrel having an outer surface, a pair of extending surfaces located distal of the barrel, a proximal end joining surface extending distally from the barrel to the pair of extending surfaces, an inner needle side locking surface extending from the outer surface of the barrel to the proximal end joining surface, in a direction traverse to a center axis of the inner needle, and a blade surface located distal of the barrel, and wherein an inner surface of the catheter comprises a catheter side locking surface extending in a direction traverse to the center axis of the inner needle, the catheter side locking surface being in contact with the inner needle side locking surface.

17. The catheter assembly according to claim 16, wherein the blade surface comprises:

a pair of proximal end inclined surfaces extending distally from the pair of extending surfaces, and a pair of distal end split surfaces extending distally from the pair of proximal end inclined surfaces to a point of the inner needle.

18. The catheter assembly according to claim 16, wherein each of the inner needle side locking surface and the catheter side locking surface is orthogonal to the center axis of the inner needle.

19. The catheter assembly according to claim 16, wherein the inner needle comprises an intermediate surface located between the inner needle side locking surface and the blade surface, and wherein the inner needle side locking surface and the intermediate surface form a recess that is recessed inward in a radial direction with respect to the barrel.

20. The catheter assembly according to claim 16, wherein an inner peripheral portion of the catheter includes a bulging portion protruding inward in a radial direction, wherein the catheter side locking surface is a surface of the bulging portion, and wherein the proximal end joining surface and the pair of extending surfaces are inclined with respect to the center axis of the inner needle.

* * * * *